(12) United States Patent
Al Shahri et al.

(10) Patent No.: US 11,860,149 B2
(45) Date of Patent: Jan. 2, 2024

(54) SYSTEMS AND METHODS FOR DYNAMIC REAL-TIME WATER-CUT MONITORING

(71) Applicant: Saudi Arabian Oil Company, Dhahran (SA)

(72) Inventors: Ali M. Al Shahri, Doha (SA); Anas A. Al Shuaibi, Dammam (SA); Mohammed S. Kanfar, Dammam (SA); Kalid Saad Dosary, Al-Khobar (SA); Abdulaziz A. Alsaleh, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 326 days.

(21) Appl. No.: 17/194,958

(22) Filed: Mar. 8, 2021

(65) Prior Publication Data

US 2021/0349071 A1 Nov. 11, 2021

Related U.S. Application Data

(60) Provisional application No. 63/022,849, filed on May 11, 2020.

(51) Int. Cl.
*G01N 33/28* (2006.01)
*G06N 3/08* (2023.01)
*E21B 49/08* (2006.01)

(52) U.S. Cl.
CPC ..... *G01N 33/2847* (2013.01); *E21B 49/0875* (2020.05); *G06N 3/08* (2013.01); *E21B 2200/20* (2020.05)

(58) Field of Classification Search
CPC ............ G01N 33/2847; E21B 49/0875; E21B 2200/20
See application file for complete search history.

(56) References Cited

U.S. PATENT DOCUMENTS 4,726,219 A 2/1988 Pearson et al.
5,597,961 A * 1/1997 Marrelli ................... G01F 1/363
73/861.04

(Continued)

OTHER PUBLICATIONS

Camilleri et al., "Obtaining Real-Time Flow Rate, Water Cut, and Reservoir Diagnostics from ESP Gauge Data", Paper SPE 145542 presented at the SPE Offshore Europe Oil and Gas Conference and Exhibition, Aberdeen, UK, Sep. 6-8, 2011.

(Continued)

*Primary Examiner* — Regis J Betsch
(74) *Attorney, Agent, or Firm* — Dinsmore & Shohl LLP

(57) ABSTRACT

Embodiments described herein include a system for dynamic real-time water-cut monitoring that includes a plurality of sensors for sensing pressure across a pipe that includes logic that causes the system to determine whether to use a direct approach for determining water-cut. In some embodiments, in response to determining not to use the direct approach, the logic causes the system to determine an initial guess for water-cut, estimate at least one dynamic pressure loss across the distance, estimate at least one potential energy pressure loss across the distance, estimate a value for water-cut from the at least one dynamic pressure loss and the at least one potential energy pressure loss, determine whether the initial guess is within a predetermined threshold of the value for water-cut, and in response to determining that the initial guess is within the predetermined threshold of the value for water-cut, output the value for water-cut.

20 Claims, 6 Drawing Sheets

(56) References Cited

U.S. PATENT DOCUMENTS

| | | |
|---|---|---|
| 6,766,854 B2 | 7/2004 | Ciglenec et al. |
| 8,244,509 B2 | 8/2012 | Banerjee et al. |
| 8,527,219 B2 | 9/2013 | Camilleri |
| 9,803,470 B2 | 10/2017 | Mashetty et al. |
| 10,072,485 B2 | 9/2018 | Machado et al. |
| 2013/0081460 A1 | 4/2013 | Xiao et al. |
| 2017/0058664 A1* | 3/2017 | Xiao ............... E21B 47/06 |
| 2020/0150634 A1 | 5/2020 | Gray et al. |

OTHER PUBLICATIONS

Al Enezi et al., "Forecasting and Monitoring Water Cut Utilizing ESP Pump Discharge Pressures and Fluid PVT Analysis", Paper SPE 160886 presented at the SPE Saudi Arabia Section Technical Symposium and Exhibition, Al-Khobar, Saudi Arabia, Apr. 8-11, 2012.

International Search Report and Written Opinion dated Jul. 5, 2021 pertaining to International application No. PCT/US2021/022292 filed Mar. 15, 2021, 17 pages.

Ünalmis, Ö. H. "Downhole Multiphase Flow Measurement in Horizontal Wellbores", SPE-164854-MS, SPE International, Jun. 10, 2013, pp. 1-15.

* cited by examiner

SYSTEMS AND METHODS FOR DYNAMIC REAL-TIME WATER-CUT MONITORING

CROSS REFERENCE

This application claim priority to U.S. Provisional Application Ser. No. 63/022,849, filed on May 11, 2020.

TECHNICAL FIELD

This application is directed to systems and methods for dynamic real-time water-cut monitoring and, more specifically, to utilizing field data to arrive at water-cut estimations.

BACKGROUND

One of the challenges the oil and gas industry faces today is water-cut (WC) monitoring. Many current solutions of WC monitoring utilize analytical based models or lab based correlations to estimate WC. This results in a poor match due to many assumptions incorporated in the analytical models and lab correlations. Additionally, some current solutions utilize expensive electrical submersible pump (ESP) sensors to directly measure WC, which are only utilized a few times per year and require extensive calibration. None of these current solutions provides a feasible approach for continuous water-cut measurements. These current solutions are either limited to ESP sensors or provide a poor match due to the many assumptions adapted.

Similarly, many conventional mechanisms for measuring WC utilize one multiphase flowmeter per drill site or platform. The wells are then flowed to the multiphase flowmeter one by one to measure WC, with each measurement taking about a day to allow the flow to stabilize. Such a setup has several problems. First, the WC measurements in this setup are not continuous, but rather intermittent, with wells being tested around one time per month depending on how many wells are connected to a single flowmeter. Second, the flowmeter itself is subject to drifting and may be off calibration unbeknownst to the operator. This may lead to misleading results and ill-informed decision making by the reservoir management team. Conventional solutions that utilize a multi-phase flowmeter for each well are also very costly. Thus, a need exists in the industry for dynamic real-time water-cut monitoring.

SUMMARY

Embodiments described herein include a system for dynamic real-time water-cut monitoring that includes a plurality of sensors for sensing pressure across a pipe that includes logic that causes the system to determine whether to use a direct approach for determining water-cut. In some embodiments, in response to determining not to use the direct approach, the logic causes the system to determine an initial guess for water-cut, estimate at least one dynamic pressure loss across the distance, estimate at least one potential energy pressure loss across the distance, estimate a value for water-cut from the at least one dynamic pressure loss and the at least one potential energy pressure loss, determine whether the initial guess is within a predetermined threshold of the value for water-cut, and in response to determining that the initial guess is within the predetermined threshold of the value for water-cut, output the value for water-cut.

Some embodiments include a method for dynamic real-time water-cut monitoring that includes determining whether to use a direct approach for determining water-cut from a pipe of an oil well. In some embodiments, the method, in response to determining not to use the direct approach performs an iterative approach. The iterative approach may include (a) determining, by the computing device, an initial guess for water-cut, (b) estimating, by the computing device, at least one dynamic pressure loss across a distance between pressure sensors, and (c) estimating, by the computing device, at least one potential energy pressure loss across the distance. In some embodiments, the iterative approach includes (d) estimating, by the computing device, a value for water-cut from the at least one dynamic pressure loss and the at least one potential energy pressure loss, (e) determining, by the computing device, whether the initial guess is within a predetermined threshold of the value for water-cut, and (f) in response to determining that the initial guess is within the predetermined threshold of the value for water-cut, outputting, by the computing device, the value for water-cut. In some embodiments, the iterative approach includes (g) in response to determining that the initial guess is not within the predetermined threshold of the value for water-cut, repeating at least one of (b)-(f) of the iterative approach to recalculate water-cut using the value for water-cut as the initial guess.

Some embodiments include a non-transitory computer-readable medium for dynamic water-cut monitoring that includes logic that, when executed by a computing device, causes the logic to (a) determine an initial guess for water-cut, (b) estimate at least one dynamic pressure loss across a distance between pressure sensors, and (c) estimate at least one potential energy pressure loss across the distance. In some embodiments the logic further causes the computing device to (d) estimate a value for water-cut from the at least one dynamic pressure loss and the at least one potential energy pressure loss, (e) determine whether the initial guess is within a predetermined threshold of the value for water-cut, and (f) in response to determining that the initial guess is within the predetermined threshold of the value for water-cut, output the value for water-cut. In some embodiments, the logic causes the computing device to: (g) in response to determining that the initial guess is not within the predetermined threshold of the value for water-cut, repeat at least one of (b)-(f) to recalculate water-cut using the value for water-cut as the initial guess.

DETAILED DESCRIPTION OF THE DISCLOSURE

Embodiments provided herein include systems and methods for providing dynamic real-time water-cut monitoring of fluid from an oil well or plurality of wells. These embodiments may utilize field data and machine learning methods to arrive at water-cut (WC) estimations. Because this approach provides superior results, new analytics and new advisories become feasible.

Some of these embodiments provide a mechanism to benchmark multi-phase flowmeters, instantly identify malfunctioning flowmeters, and optimize flowmeter calibration frequencies and schedules. These embodiments may provide a mechanism to interpolate between the often-sparse WC measurements and to automatically determine production allocation per well in real-time or near real-time. These embodiments can be implemented in many fields that utilize pressure and temperature sensors and an estimated liquid gross rate. Unlike WC, liquid gross rate can be reliably measured through flowmeters (e.g. Venturi based, Coriolis based, etc.) or estimated through artificially intelligent systems. Further, pressure and temperature can also be reliably measured at surface through wellhead sensors and at subsurface through permanent downhole gauges or electronic stability program (ESP) sensors. The systems and methods for providing dynamic real-time water-cut monitoring of fluid from a well or plurality of wells incorporating the same will be described in more detail, below.

Figure 1:
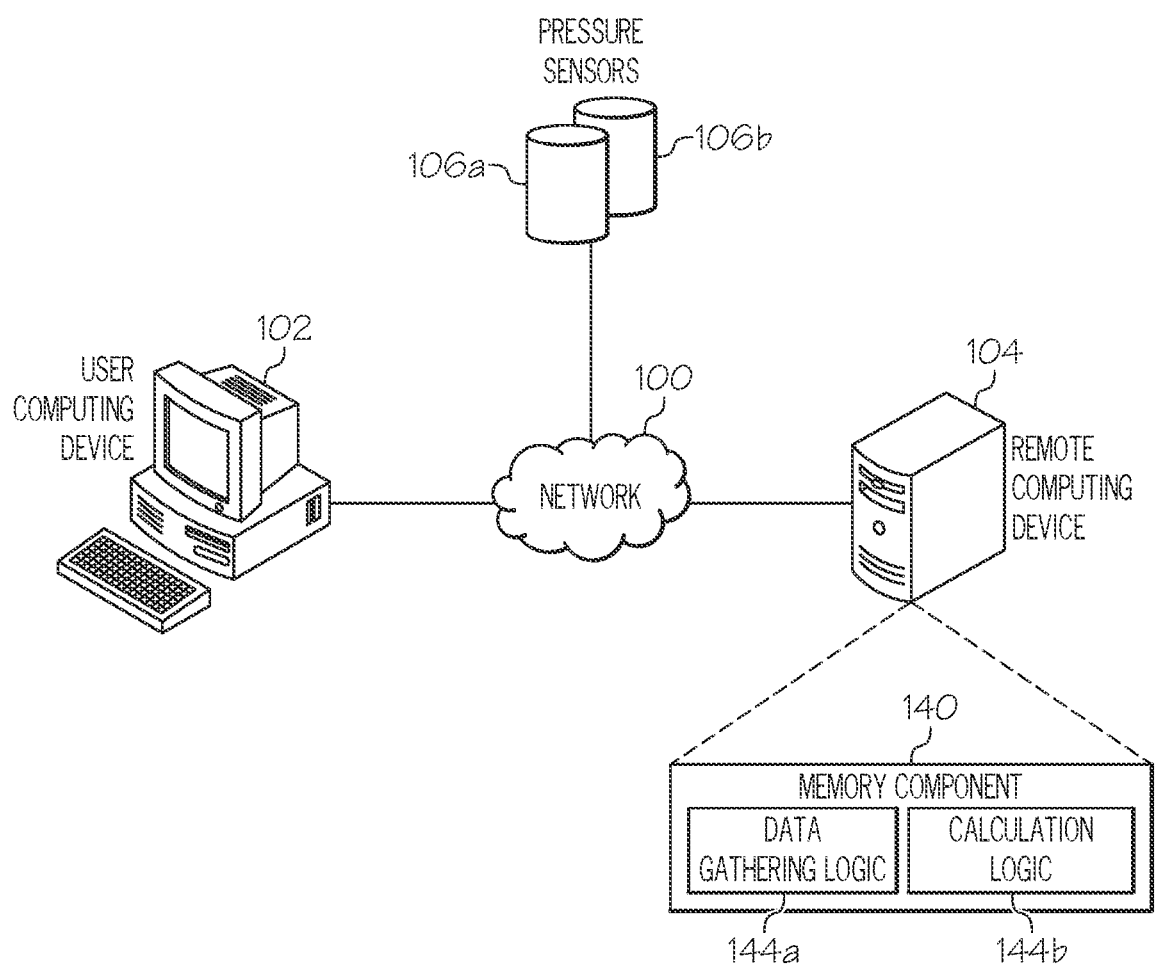
FIG. 1 depicts a computing environment for dynamic real-time water-cut monitoring, according to embodiments described herein.

Referring now to the drawings, FIG. 1 depicts a computing environment for dynamic real-time water-cut monitoring, according to embodiments described herein. As illustrated, the embodiment of FIG. 1 illustrates a network coupled to a user computing device 102 and a remote computing device 104. The network 100 may include any wide area network (such as the internet, cellular network, mobile data network, WiMax network, etc.), any local network (such as a local area network, Wi-Fi network, mesh network, etc.), and/or any peer-to-peer network (such as via Bluetooth, ZigBee, etc.). The user computing device 102 may be configured as any personal computer, laptop, mobile device, database, server, etc. for interfacing with a user and thus may include input devices and output devices for facilitating such interface. The remote computing device 104 may include any server, database, personal computer, tablet, mobile device, and/or other device for storing data described and/or performing the calculations described herein. As depicted in FIG. 1, the remote computing device 104 may include a memory component 140 that stores data gathering logic 144a and calculation logic 144b. As described in more detail below, the data gathering logic 144a may be configured for machine learning and/or as a neural net for causing a computing device to accumulate data, perform the calculations, assemble graphical depictions of wells, determine historical well data, pressure data, temperature data, flow data, etc. The calculation logic 144b may cause the computing device to perform one or more calculations described herein and/or provide output for display and/or upload.

Also depicted in FIG. 1 are an upstream pressure sensor 106a and a downstream pressure sensor 106b (collectively referred to as "pressure sensors 106"). The upstream pressure sensor 106a may be disposed at an upstream portion of the pipe 202 (FIG. 2) in a bottom hole, near the reservoir 200 (FIG. 2), while the downstream pressure sensor 106b may be disposed at a downstream portion of the pipe 202 (FIG. 2), near the surface. The pressure sensors 106 may be utilized to determine pressure readings for a well, as described in more detail below. The pressure sensors 106 may be configured as off the shelf sensors in some embodiments and/or as more sophisticated sensors in other embodiments. Similarly, the pressure sensors 106 may also represent other types of sensors, such as temperature sensors, flowmeters, etc. Similarly, while two sensors are depicted in FIG. 1, any number may be utilized, depending on the sensors and desired functionality.

It will be understood that while FIG. 1 depicts a particular network configuration, this is merely one example. Some embodiments may be configured such that the user computing device 102 performs the calculations and recommendations (and thus stores the data gathering logic 144a and/or the calculation logic 144b) and only retrieves data from the remote computing device 104.

Figure 2:
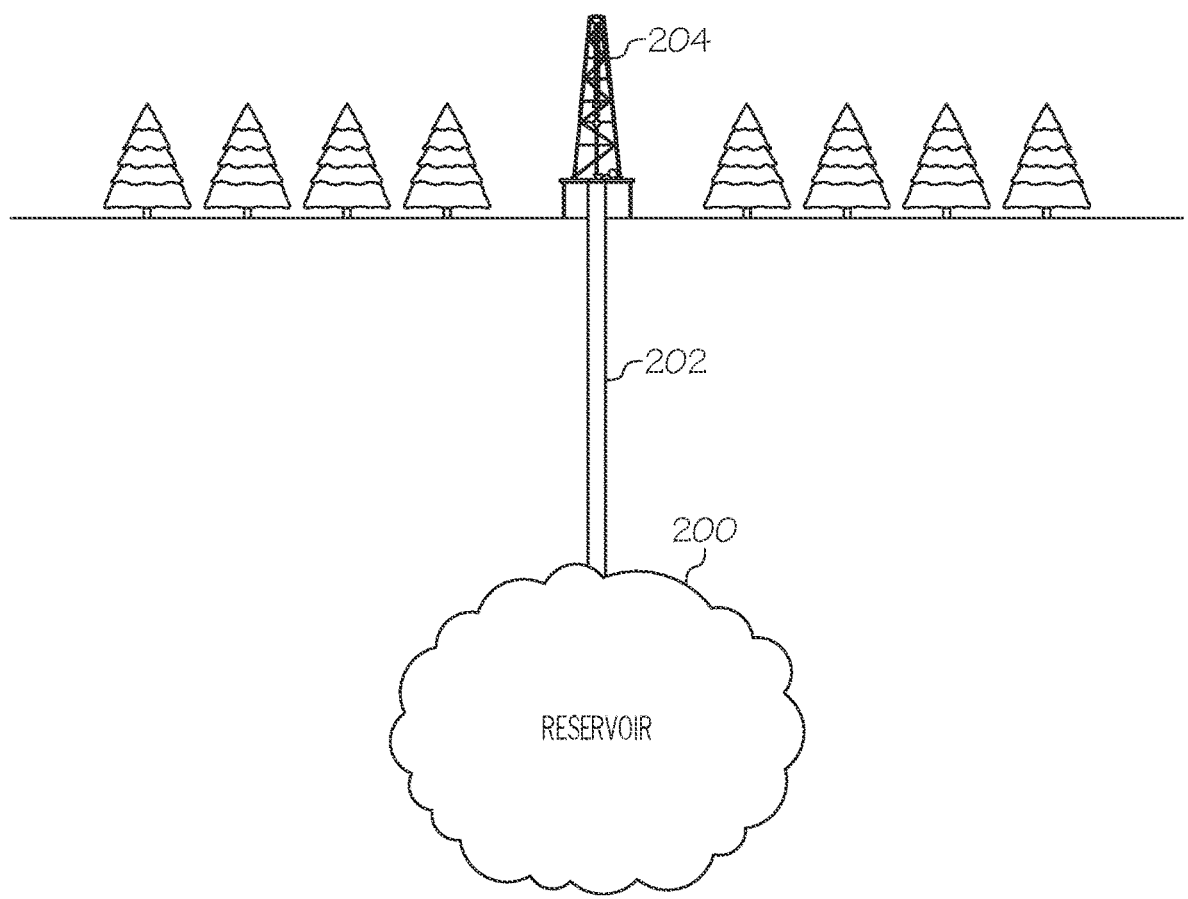
FIG. 2 depicts a reservoir that may be selected for dynamic real-time water-cut monitoring, according to embodiments described herein.

FIG. 2 depicts a reservoir 200 that may be selected for dynamic real-time water-cut monitoring, according to embodiments described herein. As illustrated, the reservoir 200 may be disposed below the ground and may include one or more different fluids including oil, natural gas, water, and/or other fluids. As such, when a well is created, a pipe 202 may be drilled into the ground to access the reservoir 200. A pump 204, which may be configured as a "Christmas tree" structure, a pump jack, and/or other apparatus may be coupled to the pipe for extracting fluid from the reservoir 200.

It will be understood that depending on the particular embodiment a plurality of wells may be utilized for a single reservoir 200. As such, a plurality of different pipes 202 and/or pumps 204 may be utilized, thus increasing the complexity of dynamic water cut monitoring.

Figure 3:
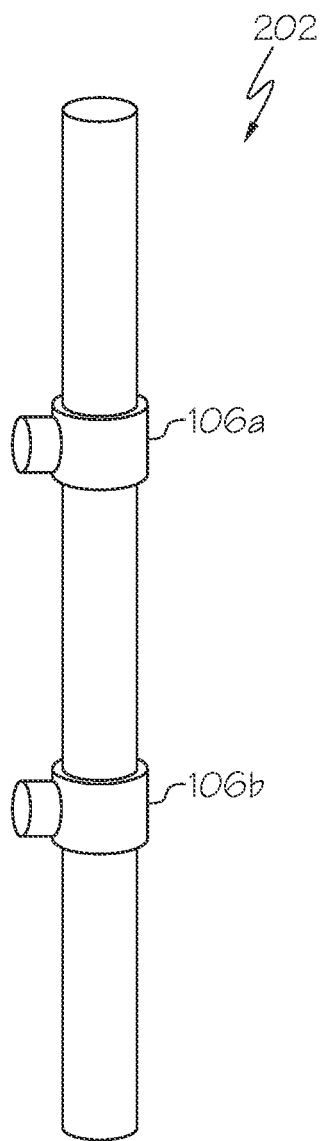
FIG. 3 depicts a pipe with pressure sensors coupled thereto for dynamic real-time water-cut monitoring, according to embodiments provided herein.

FIG. 3 depicts a pipe 202 with pressure sensors 106 coupled thereto for dynamic real-time water-cut monitoring, according to embodiments provided herein. As illustrated, a plurality of pressure sensors 106 may be disposed a predetermined distance apart in order to capture pressure readings and thus calculate pressure changes as the fluid traverses the pipe 202. As discussed above, while the sensors of FIG. 3 may be depicted as pressure sensors 106, these sensors may be configured as any type of sensors that may be utilized for performing the measurements described herein. Further, while a plurality of pressure sensors 106 is depicted in FIG. 3, this is also merely one example. Some embodiments may utilize a single device that is configured to take measurements at a plurality of positions in the pipe 202 or several devices for this purpose.

The embodiments depicted in FIGS. 1-3 may be configured to determine a pressure change from one point to another as a function of a plurality of factors, including WC. Hence, if all other factors are isolated, WC can be determined from the pressure change across two points. The learning of WC impact on pressure change between two sensors may be accomplished via machine learning of large scrutinized datasets or via other mechanisms. In general, the pressure drop across two points for incompressible fluids can be broken down to pressure losses due to potential energy (PE), kinetic energy (KE), and friction (F) as per the following equation: $\Delta p = \Delta p_{PE} + \Delta p_{KE} + \Delta p_F$.

In many cases, pressure loss due to kinetic energy can be ignored because the diameter of the pipe 202 between the pressure sensors 106 is often constant. On the other hand, frictional pressure loss is often significant and may be accounted, especially when the distance between the pressure sensors 106 is large.

In many current solutions, frictional pressure losses are estimated from physical models or lab-based correlations. This conventional approach limits estimate accuracy because field conditions may differ from ideal models or lab conditions. In contrast, frictional pressure loss described herein may be estimated based on a data-driven machine learning approach. Some of the parameters that correlate to frictional pressure losses are gross rate, an area of the pipe 202, length in measured depth, WC, and/or fluid properties. Other parameters that can be indicative of WC and are included in machine learning, if available, are ESP parameters (e.g., Volts, Amps, horsepower, speed, motor temperature, discharge temperature, number of stages, etc.). It will be understood that in some cases when the distance between sensors is small and/or pipe diameter is large, frictional effects may be negligible. Additionally, the pressure losses due to potential energy (PE) can be estimated via the following equation:

$\Delta p_{PE}=(1-WC)g_o h_{TVD}+WC\, g_w h_{TVD}$, where $g_o$ refers to a gravity of oil; $h_{TVD}$ refers to total vertical depth difference between the pressure sensors 106; and $g_w$ refers to the gravity of water.

As presented above, one challenge for calculating pressure drop across two points is the calculation of frictional pressure losses and if applicable kinetic pressure losses. Embodiments described herein utilize machine learning to determine frictional and kinetic pressure losses, based on historical data associated with measured frictional and/or kinetic losses of similar systems, and/or calculated and verified frictional and/or kinetic losses. Once all pressure losses are reliably modeled, WC can be inverse determined. These embodiments receive a sufficient amount of data points from real-time data and a sufficient amount of reliable historical water-cut measurements (e.g. via separator testing, sampling, a well-calibrated meter). These points may be used as the truth model for data training.

Using reliable historical WC measurements via a truth model, embodiments described herein estimate pressure losses due to potential energy using the following equation:

$\Delta p_{PE}=(1-WC)g_o h_{TVD}+WC\, g_w h_{TVD}$, where $WC$ is a fraction.

Some embodiments described herein calculate the pressure losses due to friction and kinetic energy, henceforth called dynamic energy losses, as follows:

$\Delta p_{Dyn}=\Delta p_F+\Delta p_{KE}=p_{downstream}-p_{upstream}\Delta p_{PE}$, where $p_{downstream}$ represents the pressure reading from the downstream pressure sensor 106b and $p_{upstream}$ represents the pressure reading from the upstream pressure sensor 106a.

As mentioned above, pressure losses due to kinetic energy are often negligible. Accordingly, embodiments described herein may utilize machine learning to relate at least one dynamic pressure loss (or dynamic pressure losses) to parameters such as gross rate, pressure at the two gauges, temperature at the two gauges, distance between gauges in measured depth, pipe area, and fluid properties and if applicable volts, amps, horsepower, motor speed, motor temperature, discharge temperature, and number of stages. It should be understood that multi-variate nonlinear regression and/or deep learning may be used.

If a match is obtained without including WC, embodiments herein may utilize the direct approach. In other words, if dynamic pressure losses are independent of WC (e.g., WC may be neglected in the dynamic pressure losses calculation), WC may be directly calculated from the equations above. Specifically, the direct approach utilizes the machine learning algorithm to estimate the dynamic pressure losses. One can estimate the $\Delta p_{PE}$ as follows: $\Delta p_{PE}=p_{downstream}-p_{upstream}-\Delta p_F-\Delta p_{KE}$. As such, in the direct approach, WC can be estimated by re-arranging the following equation: $\Delta p_{PE}=(1-WC)g_o h_{TVD}+WC\, g_w h_{TVD}$.

If a match is not obtained, embodiments may utilize an iterative approach or iterative process. When utilizing the iterative approach, embodiments start with an initial guess of water-cut ($WC_i$). Using $WC_i$ and the other known parameters, embodiments estimate the dynamic pressure losses. Embodiments may then estimate $\Delta p_{PE}$ as follows: $\Delta p_{PE}=p_{downstream}-p_{upstream}-\Delta p_F-\Delta p_{KE}$. Next, embodiments may estimate WC by re-arranging the following equation: $\Delta p_{PE}=(1-WC)g_o h_{TVD}+WC\, g_w h_{TVD}$. If the initial guess is within a predetermined threshold of WC (such as $WC_i$ 0.001 of WC, $WC_i<0.01$ of WC, or other predetermined threshold) the process stops, otherwise WC is used as the new guess $WC_i$=WC and the process repeats.

Accordingly, embodiments described herein provide a continuous WC estimate in real-time or near-real time, as well as provide a mechanism to benchmark multi-phase flowmeters. Embodiments may provide a mechanism to instantly identify malfunctioning flowmeters and a mechanism to optimize flowmeter calibration frequencies and schedule. Some embodiments provide a mechanism to interpolate between the often-sparse WC measurements, as well as a mechanism to automatically determine production allocation per well in real-time.

Some embodiments described herein can be implemented in many fields, as these embodiments may only utilize pressure and temperature sensors and an estimated liquid gross rate. Some embodiments may be utilized to flag meters that are due for calibration. This will not only enhance the measurement quality of existing meters, but will also optimize cost by optimizing calibration frequency from periodic calibration to as-needed-basis calibration.

Figure 4:
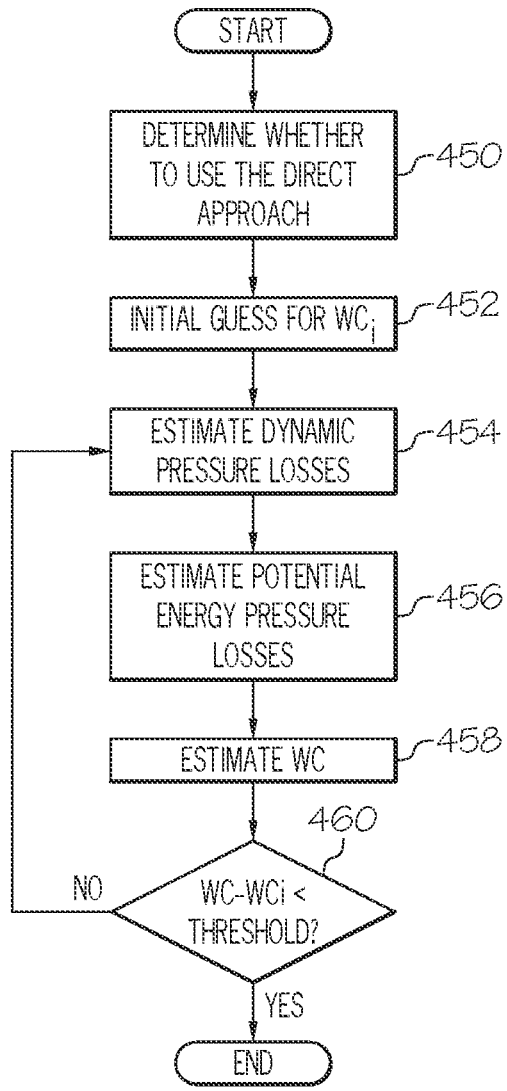
FIG. 4 depicts a flowchart for dynamic real-time water-cut monitoring, according to embodiments provided herein.

FIG. 4 depicts a flowchart for dynamic real-time water-cut monitoring, according to embodiments provided herein. As illustrated in block 450, a determination may be made regarding whether to use the direct approach or the iterative approach. As discussed above, this determination may be made based on whether dynamic pressure losses may be calculated without using a WC value and/or via other mechanisms, such as time needed for a solution, preference of the user, and/or for other reasons. If the direct approach is desired, WC may be calculated, as described above. If the direct approach is not desired (and/or if the indirect approach is desired), at block 452, an initial guess for $WC_i$ may be determined. The guess $WC_i$ may be made from historical values for WC from machine learning algorithms based on sensor data, and/or via other mechanisms.

At block 454, dynamic pressure losses may be estimated. As described above, dynamic pressure losses may be estimated using the formula above, with the pressure data from the pressure sensors 106. At block 456, at least one potential energy pressure loss (or potential energy pressure losses) may be estimated. Again, the potential energy pressure losses may be calculated from $\Delta p_{PE}=p_{downstream}-p_{upstream}-\Delta p_F\Delta p_{KE}$. In block 458, WC may be estimated by solving the following for WC $\Delta p_{PE}=(1-WC)g_o h_{TVD}WC\, g_w h_{TVD}$. If in block 460, $WC-WC_i$ is <0.001, the process may end. If not, the process may return to block 454, using this iteration WC for $WC_i$.

Figure 5:
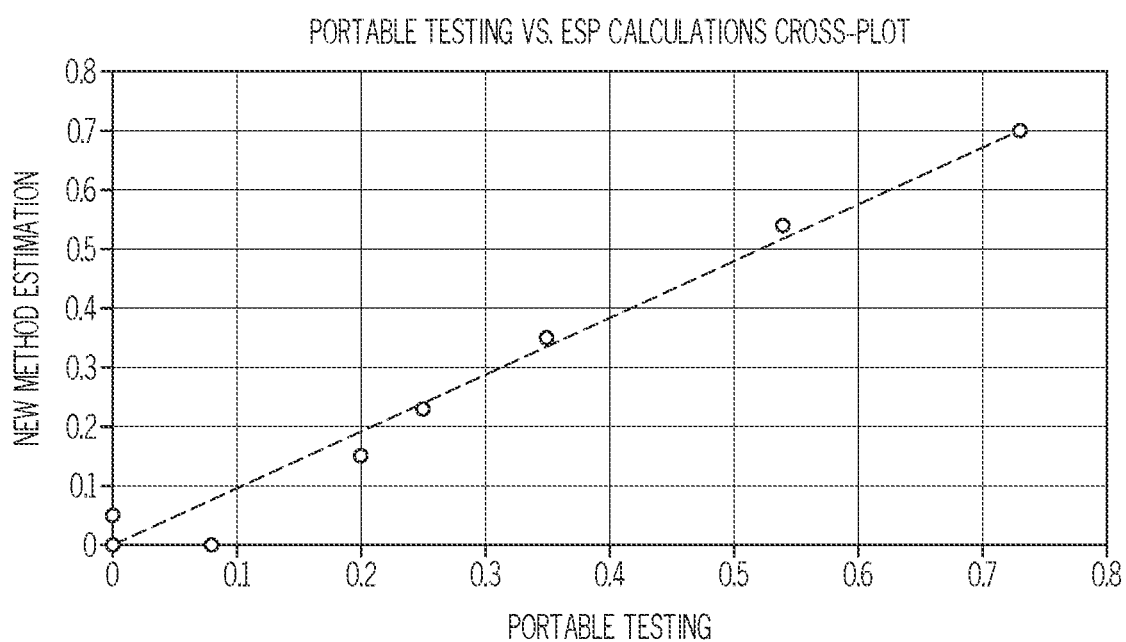
FIG. 5 depicts a graph of portable testing versus new method estimation, as provided in embodiments described herein.

FIG. 5 depicts a graph of portable testing versus new method estimation, as provided in embodiments described herein. As illustrated, there is a roughly linear relationship between new method estimation and portable testing. Specifically, new method estimation may range from about 0 to about 0.8 and portable testing may range from about 0 to about 0.8.

Figure 6:
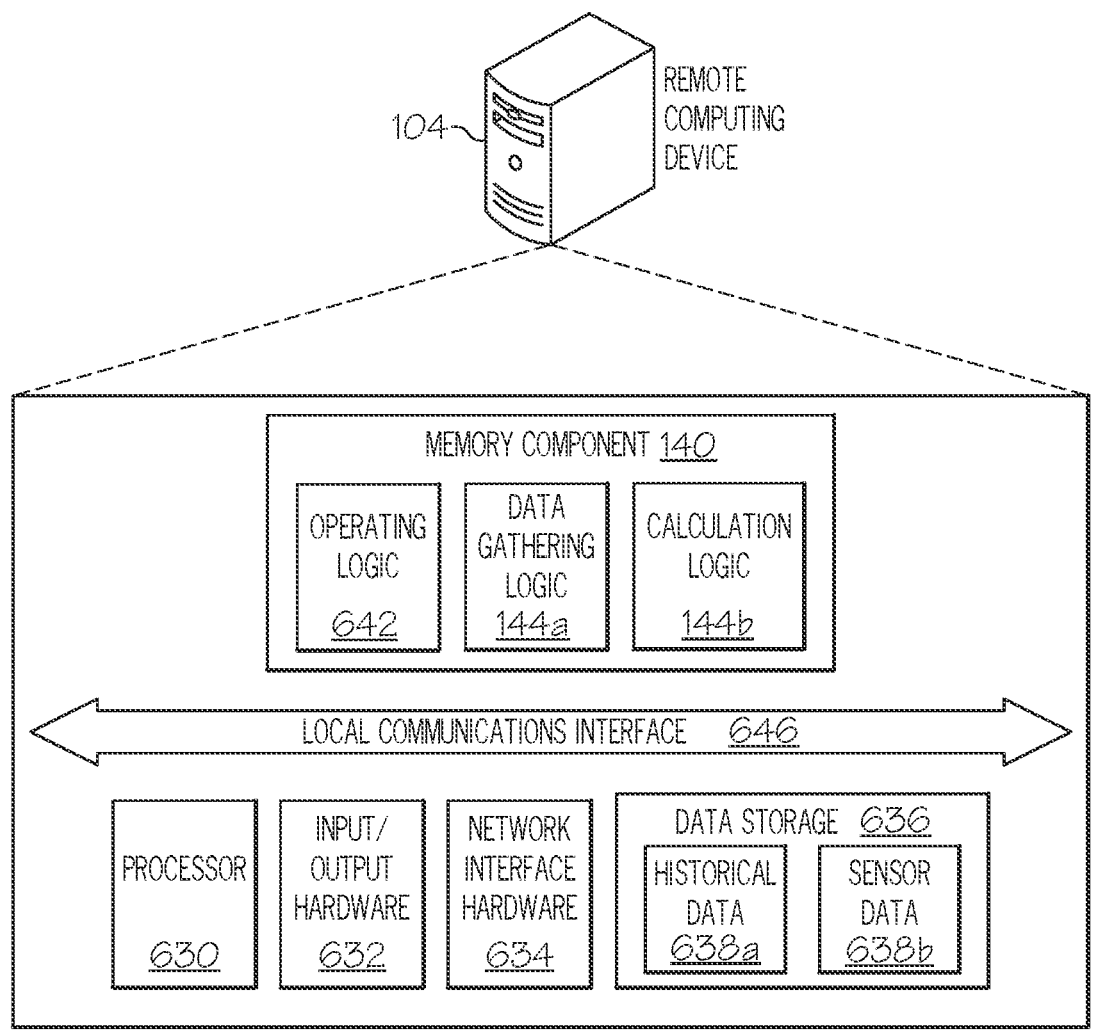
FIG. 6 depicts a computing device for dynamic real-time water-cut monitoring, according to embodiments described herein.

FIG. 6 depicts a computing device for dynamic real-time water-cut monitoring, according to embodiments described herein. As illustrated, the remote computing device 104 includes a processor 630, input/output hardware 632, a network interface hardware 634, a data storage component 636 (which stores production data 638a and/or other data 638b as described with reference to FIG. 2), and a memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD) (whether local or cloud-based), and/or other types of non-transitory computer-readable medium. Depending on the particular embodiment, these non-transitory computer-readable mediums may reside within the remote computing device 104 and/or external to the remote computing device 104.

The memory component 140 may store operating logic 642, the data gathering logic 144a, and the calculation logic 144b. Each of these logic components may include a plurality of different pieces of logic, each of which may be embodied as a computer program, firmware, and/or hardware, as an example. A local interface 646 is also included in FIG. 6 and may be implemented as a bus or other communication interface to facilitate communication among the components of the remote computing device 104.

The processor 630 may include any processing component operable to receive and execute instructions (such as from a data storage component 636 and/or the memory component 140). As described above, the input/output hardware 632 may include and/or be configured to interface with speakers, microphones, and/or other input/output components.

The network interface hardware 634 may include and/or be configured for communicating with any wired or wireless networking hardware, including an antenna, a modem, a LAN port, wireless fidelity (Wi-Fi) card, WiMAX card, mobile communications hardware, and/or other hardware for communicating with other networks and/or devices. From this connection, communication may be facilitated between the remote computing device 104 and other computing devices.

The operating logic 642 may include an operating system and/or other software for managing components of the remote computing device 104. As discussed above, the data gathering logic 144a may include machine learning characteristics and/or be configured as a neural net. The data gathering logic 144a may reside in the memory component 140 and may be configured to cause the processor 630 to gather data, create models based on historical data, predict future values based on the historical data, and/or perform similar functions. The calculation logic 144b may be configured to cause the processor 630 to perform the calculations described herein for acquiring the water-cut data, perform other calculations, and/or output results to a display device or other output device.

It should be understood that while the components in FIG. 6 are illustrated as residing within the remote computing device 104, this is merely an example. In some embodiments, one or more of the components may reside external to the remote computing device 104 or within other devices, such as the user computing device 102 depicted in FIG. 1. It should also be understood that, while the remote computing device 104 is illustrated as a single device, this is also merely an example. In some embodiments, the data gathering logic 144a and the calculation logic 144b may reside on different computing devices.

As an example, one or more of the functionalities and/or components described herein may be provided by the remote computing device 104 and/or the user computing device 102. Depending on the particular embodiment, any of these devices may have similar components as those depicted in FIG. 6. To this end, any of these devices may include logic for performing the functionality described herein.

Additionally, while the remote computing device 104 is illustrated with the data gathering logic 144a and the calculation logic 144b as separate logical components, this is also an example. In some embodiments, a single piece of logic may provide the described functionality. It should also be understood that while the data gathering logic 144a and the calculation logic 144b are described herein as the logical components, this is also an example. Other components may also be included, depending on the embodiment.

As illustrated above, various embodiments for dynamic real-time water-cut monitoring are disclosed. These embodiments may be configured to provide continuous, regular, periodic, on-demand, or other type of water-cut reporting. Additionally, these embodiments do not require expensive sensors, cut off the shelf pressure sensors that are easily calibrated and maintained. Further, these embodiments can also provide ultra-fast monitoring or more robust reporting, depending on the particular desires of the system and/or user. This invention provides a continuous WC estimate at the wellhead in real-time. Some embodiments provide a mechanism to benchmark multi-phase flowmeters, instantly identify malfunctioning flowmeters, optimize flowmeter calibration frequencies and schedules, interpolate between the often-sparse WC measurements, automatically determine production allocation per well in real-time. Some embodiments may utilize the functionality described herein in many fields as it only requires pressure and temperature sensors and an estimated liquid gross rate.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for dynamic real-time water-cut monitoring. It should also be understood that these embodiments are merely exemplary and are not intended to limit the scope of this disclosure.

What is claimed is:

1. A system for dynamic real-time water-cut monitoring comprising:
    a plurality of sensors for sensing pressure across a pipe, wherein each of the plurality of sensors is separated by a common distance from a next sensor of the plurality of sensors along the pipe, wherein the pipe facilitates the transfer of fluid, wherein the fluid includes water; and
    a computing device that includes a memory component that stores logic that, when executed by the computing device, causes the system to perform at least the following:
        determine whether to use a direct approach for determining water-cut; and
        in response to determining not to use the direct approach:
            determine an initial guess for water-cut;
            estimate, from an output of two sensors of the plurality of sensors, at least one dynamic pressure loss between the two sensors;

estimate, from the output of the two sensors, at least one potential energy pressure loss between the two sensors;

estimate a value for water-cut from the at least one dynamic pressure loss and the at least one potential energy pressure loss;

determine whether the initial guess is within a predetermined threshold of the value for water-cut; and in response to determining that the initial guess is within the predetermined threshold of the value for water-cut, output the value for water-cut.

2. The system of claim 1, wherein the logic further causes the system to perform, in response to determining that the initial guess is not within the predetermined threshold of the value for water-cut, perform an iterative process to recalculate water-cut using the value for water-cut as the initial guess.

3. The system of claim 1, wherein in response to determining to utilize the direct approach the logic causes the system to perform at least the following:

calculate a change in pressure from potential energy $(\Delta p_{PE})$ as follows: $\Delta p_{PE} = p_{downstream} - p_{upstream} - \Delta p_F - \Delta p_{KE}$, wherein $p_{downstream}$ refers to pressure at a downstream portion of the pipe, wherein $p_{upstream}$ refers to pressure at an upstream portion of the pipe, wherein $\Delta p_F$ refers to the change in pressure resulting from friction, wherein $\Delta p_{KE}$ refers to a change in pressure resulting from kinetic energy; and estimate water-cut from the following equation: $\Delta p_{PE} = (1-WC)g_o h_{TVD} + WC\ g_w h_{TVD}$, wherein $g_o$ refers to a gravity of oil, wherein $g_w$ refers to a gravity of water, wherein $h_{TVD}$ refers to a total vertical depth difference between measurements.

4. The system of claim 3, wherein calculating $(\Delta p_{PE})$ includes utilizing a truth model that was created using historical water-cut data.

5. The system of claim 3, wherein $\Delta p_F$ is determined from at least one of the following: a gross rate, an area of the pipe, a length in measured depth, WC, fluid properties, Volts, Amps, horsepower, speed, motor temperature, discharge temperature, or a number of stages.

6. The system of claim 1, wherein estimating change in pressure resulting from potential energy $(\Delta p_{PE})$ includes utilizing the following: $\Delta p_{PE} = p_{downstream} - p_{upstream} - \Delta p_F - \Delta p_{KE}$, wherein $p_{downstream}$ refers to pressure at a downstream portion of the pipe, wherein $p_{upstream}$ refers to pressure at an upstream portion of the pipe, wherein $\Delta p_F$ refers to a change in pressure resulting from friction, wherein $\Delta p_{KE}$ refers to a change in pressure resulting from kinetic energy.

7. The system of claim 1, wherein estimating water-cut includes rearranging the following equation: $\Delta p_{PE} = (1-WC)g_o h_{TVD} + WC\ g_w h_{TVD}$, wherein WC refers to water-cut, wherein $g_o$ refers to a gravity of oil, wherein $g_w$ refers to a gravity of water, wherein $h_{TVD}$ refers to a total vertical depth difference between measurements, and wherein $\Delta p_{PE}$ refers to change in pressure resulting from potential energy.

8. The system of claim 1, wherein estimating at least one dynamic pressure loss $(\Delta p_{Dyn})$ includes utilising the following equation: $\Delta p_{Dyn} = \Delta p_F + \Delta p_{KE} = p_{downstream} - p_{upstream} - \Delta p_{PE}$, wherein $p_{downstream}$ refers to pressure at a downstream portion of the pipe, wherein $p_{upstream}$ refers to pressure at an upstream portion of the pipe, wherein $\Delta p_F$ refers to a change in pressure resulting from friction, wherein $\Delta p_{KE}$ refers to a change in pressure resulting from kinetic energy, wherein $\Delta p_{PE}$ refers to a change in pressure resulting from potential energy.

9. The system of claim 1, wherein the pipe is part of an oil well and wherein the fluid further includes oil.

10. The system of claim 1, wherein the logic further causes the system to acquire historical water-cut measurements for training a truth model.

11. The system of claim 1, wherein the predetermined threshold is about 0.001.

12. A method for dynamic real-time water-cut monitoring, comprising:

determining, by a computing device, whether to use a direct approach for determining water-cut from a pipe of an oil well; and in response to determining not to use the direct approach performing an iterative process that includes:
(a) determining, by the computing device, an initial guess for water-cut;
(b) estimating, by the computing device, at least one dynamic pressure loss across a distance between two pressure sensors;
(c) estimating, by the computing device, at least one potential energy pressure loss across the distance between the two sensors;
(d) estimating, by the computing device, a value for water-cut from the at least one dynamic pressure loss and the at least one potential energy pressure loss;
(e) determining, by the computing device, whether the initial guess is within a predetermined threshold of the value for water-cut;
(f) in response to determining that the initial guess is within the predetermined threshold of the value for water-cut, outputting, by the computing device, the value for water-cut; and
(g) in response to determining that the initial guess is not within the predetermined threshold of the value for water-cut, repeating, by the computing device, (b)-(f) of the iterative approach to recalculate water-cut using the value for water-cut as the initial guess.

13. The method of claim 12, further comprising, in response to determining to utilize the direct approach:

calculating a change in pressure from potential energy $(\Delta p_{PE})$ as follows: $\Delta p_{PE} = p_{downstream} - p_{upstream} - \Delta p_F - \Delta p_{KE}$, wherein $p_{downstream}$ refers to pressure at a downstream portion of the pipe, wherein $p_{upstream}$ refers to pressure at an upstream portion of the pipe, wherein $\Delta p_F$ refers to a change in pressure resulting from friction, wherein $\Delta p_{KE}$ refers to a change in pressure resulting from kinetic energy; and estimating water-cut from the following equation: $\Delta p_{PE} = (1-WC)g_o h_{TVD}\ WC\ g_w h_{TVD}$, wherein $g_o$ refers to a gravity of oil, wherein $g_w$ refers to a gravity of water, wherein $h_{TVD}$ refers to a total vertical depth difference between measurements, wherein calculating $(\Delta p_{PE})$ includes utilising a truth model that was created using historic al water-cut data, and wherein $\Delta p_F$ is determined from at least one of the following: gross rate, area of the pipe, length in measured depth, WC, fluid properties, Volts, Amps, horsepower, speed, motor temperature, discharge temperature, or number of stages.

14. The method of claim 12, wherein estimating change in pressure resulting from potential energy $(\Delta p_{PE})$ includes utilizing the following: $\Delta p_{PE} = p_{downstream} - p_{upstream} - \Delta p_F - \Delta p_{KE}$, wherein $p_{downstream}$ refers to pressure at a downstream portion of the pipe, wherein Pup stream refers to pressure at an upstream portion of the pipe, wherein $\Delta p_F$ refers to a change in pressure resulting from friction, wherein $\Delta p_{KE}$ refers to a change in pressure resulting from kinetic energy.

15. The method of claim 12, wherein estimating water-cut includes rearranging the following equation: $\Delta p_{PE}$=(1−WC)$g_o h_{TVD}$+WC $g_w h_{TVD}$, wherein WC refers to water-cut, wherein $g_o$ refers to a gravity of oil, wherein $g_w$ refers to a gravity of water, wherein $h_{TVD}$ refers to a total vertical depth difference between measurements, and wherein $\Delta p_{PE}$ refers to change in pressure resulting from potential energy.

16. The method of claim 12, wherein estimating at least one dynamic pressure loss ($\Delta p_{Dyn}$) includes utilizing the following equation: $\Delta p_{Dyn}=\Delta p_F+\Delta p_{KE}=p_{downstream}-p_{upstream}-\Delta p_{PE}$, wherein $p_{downstream}$ refers to pressure at a downstream portion of the pipe, wherein $p_{upstream}$ refers to pressure at an upstream portion of the pipe, wherein $\Delta p_F$ refers to a change in pressure resulting from friction, wherein $\Delta p_{KE}$ refers to a change in pressure resulting from kinetic energy, wherein $\Delta p_{PE}$ refers to a change in pressure resulting from potential energy.

17. The method of claim 12, further comprising acquiring historical water-cut measurements for training a truth model.

18. The method of claim 12, wherein the predetermined threshold is about 0.001.

19. A non-transitory computer-readable medium for dynamic water-cut monitoring that includes logic that, when executed by a computing device, causes the computing device to perform at least the following:
   (a) determine an initial guess for water-cut;
   (b) estimate at least one dynamic pressure loss across a distance between pressure two sensors;
   (c) estimate at least one potential energy pressure loss across the distance between the two sensors;
   (d) estimate a value for water-cut from the at least one dynamic pressure loss and the at least one potential energy pressure loss;
   (e) determine whether the initial guess is within a predetermined threshold of the value for water-cut;
   (f) in response to determining that the initial guess is within the predetermined threshold of the value for water-cut, output the value for water-cut; and
   (g) in response to determining that the initial guess is not within the predetermined threshold of the value for water-cut, repeat (b)-(f) to recalculate water-cut using the value for water-cut as the initial guess.

20. The non-transitory computer-readable medium of claim 19, wherein the logic further causes the computing device to acquire historical water-cut measurements for training a truth model.

* * * * *